(12) United States Patent
Modtland et al.

(10) Patent No.: US 9,085,594 B2
(45) Date of Patent: Jul. 21, 2015

(54) ORGANOMETALLIC COMPOUND PURIFICATION

(75) Inventors: Curtis D. Modtland, Lake Jackson, TX (US); Chet D. Davidson, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 48 days.

(21) Appl. No.: 13/549,407

(22) Filed: Jul. 13, 2012

(65) Prior Publication Data

US 2013/0184481 A1 Jul. 18, 2013

Related U.S. Application Data

(60) Provisional application No. 61/507,355, filed on Jul. 13, 2011.

(51) Int. Cl.

| | | |
|---|---|---|
| C07F 9/00 | (2006.01) | |
| C07F 5/00 | (2006.01) | |
| C07F 3/00 | (2006.01) | |
| B01D 3/02 | (2006.01) | |
| C07F 9/90 | (2006.01) | |
| C07F 5/06 | (2006.01) | |
| C07F 3/06 | (2006.01) | |
| C07F 9/94 | (2006.01) | |
| C07F 9/72 | (2006.01) | |
| B01D 3/14 | (2006.01) | |

(52) U.S. Cl.
CPC . *C07F 9/94* (2013.01); *B01D 3/143* (2013.01); *C07F 3/06* (2013.01); *C07F 5/00* (2013.01); *C07F 5/062* (2013.01); *C07F 5/063* (2013.01); *C07F 9/723* (2013.01); *C07F 9/904* (2013.01)

(58) Field of Classification Search
USPC .................. 556/1, 70, 129, 187; 202/154
See application file for complete search history.

(56) References Cited

U.S. PATENT DOCUMENTS

| | | | |
|---|---|---|---|
| 3,016,396 A | 1/1962 | Irie et al. | |
| 4,251,453 A | 2/1981 | Garrison | |
| 4,925,962 A | 5/1990 | Beard et al. | |
| 4,948,906 A | 8/1990 | Beard | |
| 5,951,820 A | 9/1999 | Ohsaki et al. | |
| 6,495,707 B1 | 12/2002 | Leese et al. | |
| 7,112,691 B2 | 9/2006 | Tsudera et al. | |
| 7,166,734 B2 | 1/2007 | Shenai-Khatkhate et al. | |
| 7,179,931 B2 | 2/2007 | Tsudera et al. | |
| 8,101,787 B2 | 1/2012 | Lipiecki et al. | |
| 2005/0283016 A1 | 12/2005 | Tsudera et al. | |
| 2013/0184480 A1* | 7/2013 | Modtland et al. ............... 556/51 |
| 2013/0211117 A1 | 8/2013 | Modtland et al. | |
| 2013/0211118 A1 | 8/2013 | Dixit et al. | |

FOREIGN PATENT DOCUMENTS

| | | |
|---|---|---|
| CN | 1872861 A | 12/2006 |
| CN | 1872862 A | 12/2006 |
| EP | 2 280 015 A1 | 2/2011 |
| JP | 3215195 | 7/2001 |
| WO | 9740053 A1 | 10/1997 |
| WO | WO 02/07848 A1 | 1/2002 |

OTHER PUBLICATIONS

European Search Report of corresponding European Application No. 12 17 6092.

* cited by examiner

*Primary Examiner* — Porfirio Nazario Gonzalez
(74) *Attorney, Agent, or Firm* — S. Matthew Cairns

(57) ABSTRACT

A method of purifying crude organometallic compounds using a plurality of distillation columns is provided. This method effectively removes both relatively more volatile impurities and relatively less volatile impurities as compared to the organometallic compound.

19 Claims, 1 Drawing Sheet

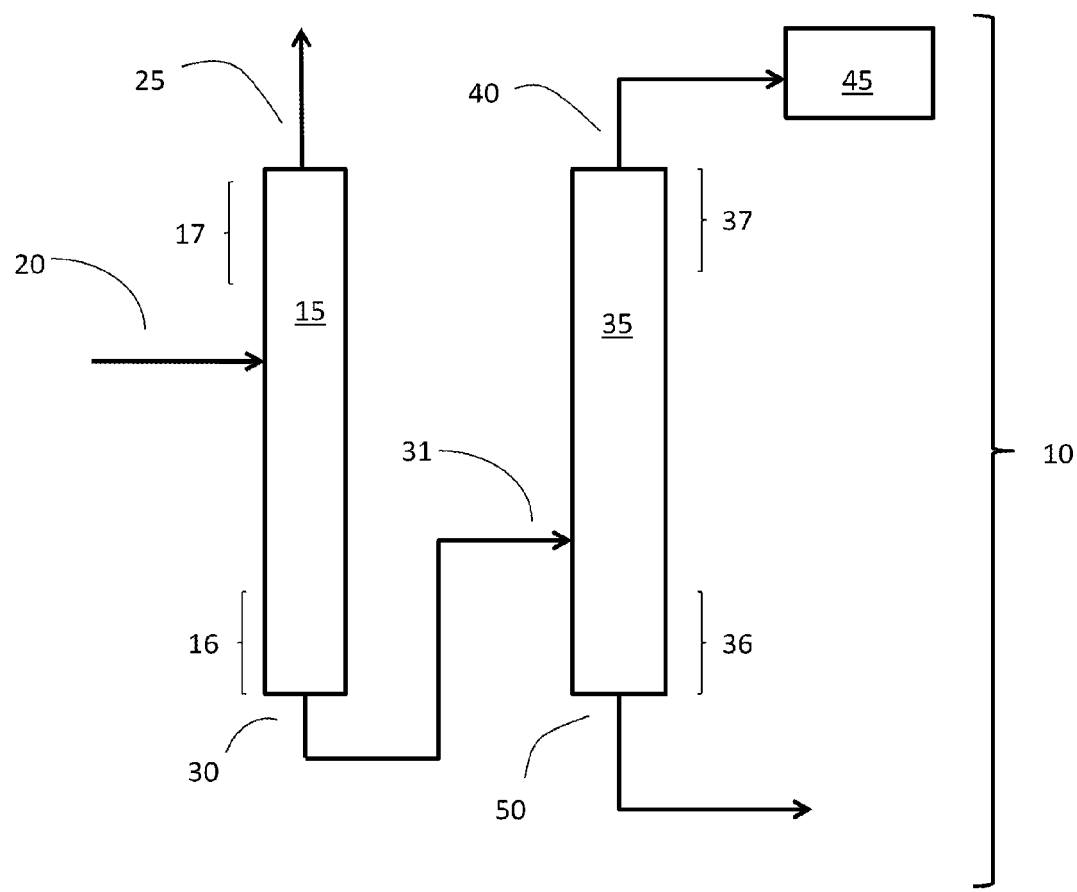

ORGANOMETALLIC COMPOUND PURIFICATION

This application claims the benefit of priority under 35 U.S.C. §119(e) to U.S. Provisional Application No. 61/507,355, filed Jul. 13, 2011, the entire contents of which application are incorporated herein by reference.

The present invention relates to the field of metal-containing compounds and particularly to the field of purifying metal-containing compounds.

Metal-containing compounds are used in a variety of applications, such as catalysts and sources for growing metal films. One use of such compounds is in the manufacture of electronic devices such as semiconductors. Many semi-conducting materials are manufactured using well-established deposition technologies that employ ultrapure metalorganic (organometallic) compounds, for example, metalorganic vapor phase epitaxy, metalorganic molecular beam epitaxy, metalorganic chemical vapor deposition and atomic layer deposition. To be useful in these processes the organometallic compounds must be free from contaminants and/or deleterious impurities. If not removed, such impurities present in the organometallic sources can cause adverse effects on the electronic and/or optoelectronic properties of electronic devices.

Crude organometallic compounds typically contain various impurities resulting from reaction byproducts, impurities in starting materials, residual solvent, or any combination of these. Such impurities are often very difficult to remove from the desired organometallic compound. Various methods have been used to purify such crude organometallic compounds.

Distillation of a single batch of organometallic compound using a single distillation column is commonly used to purify crude organometallic compounds. This conventional distillation procedure is often ineffective in removing impurities, requiring an organometallic compound to be distilled multiple times to try to obtain the organometallic compound in the desired purity. Also, due to the difficulty in separating relatively lower boiling impurities from the organometallic compound, the forerun from each distillation step is discarded. Such forerun usually contains a large amount of the organometallic compound, such as up to 30-40% of the total organometallic compound being distilled. When multiple distillations are used, the loss of organometallic compound due to the discarding of the forerun becomes very significant, which greatly increases the cost and manufacturing time of the organometallic compound.

U.S. Pat. No. 7,179,931 discloses purifying trimethylaluminum ("TMA") by distilling crude TMA from metallic sodium and collecting purified TMA as the distillate. Such distillation is preferably performed using a packed column with 10 trays or more, but not greater than 30 trays. This patent states that this distillation can be repeated several times in order to stably obtain high-purity TMA. Such a process is not attractive as it uses metallic sodium, which presents various safety concerns, and because it requires repeating the distillation step several times, including the step of collecting purified TMA, in order to stably obtain high-purity TMA.

U.S. Pat. No. 5,951,820 discloses a method for purifying certain solid organometallic compounds containing a trivalent or divalent metal atom, such as trimethylindium. In this process, the organometallic compound is evaporated and passes into a heat exchanger which is cooled such that the organometallic compound precipitates on the inner wall of the heat exchanger. The heat exchanger is then heated in order to evaporate the organometallic compound, which is then conveyed to another heat exchanger and the precipitation and evaporation process is repeated. This process is not commercially attractive as it applies only to certain solid organometallic compounds and it is very slow, requiring repeated precipitation and evaporation steps.

There remains a need to provide organometallic compounds in very high purity and in high overall yield and without the use of reactive metals.

The present invention provides a method of continuously purifying an organometallic compound comprising: (a) providing a distillation apparatus comprising a first column and a second column, each column having an upper portion and a lower portion; (b) providing a crude organometallic compound to be purified to the first distillation column; (c) subjecting the organometallic compound in the first distillation column to conditions sufficient to remove relatively more volatile impurities from the upper portion of the first distillation column; (d) conveying the organometallic compound from the lower portion of the first distillation column to the second distillation column; and (e) subjecting the organometallic compound in the second distillation column to conditions sufficient to collect purified organometallic compound from the upper portion of the second distillation column; wherein the first distillation column has a number of theoretical stripping stages sufficient to remove of the relatively more volatile impurities from the organometallic compound; wherein the second distillation column has a number of theoretical rectification stages sufficient to obtain purified organometallic compound; and wherein the obtained purified organic compound has a purity of ≥95%.

Also provided by the present invention is an apparatus adapted for continuous distillation of an organometallic compound comprising: a source of crude organometallic compound; a first distillation column having an inlet for receiving the crude organometallic compound, an upper portion having an outlet for removing impurities, and a lower portion having an outlet for removing organometallic compound; a second distillation column having an inlet for receiving organometallic compound, an upper portion having an outlet in fluid communication with a receiver for receiving purified organometallic compound, and a lower portion having an outlet; the outlet in the lower portion of the first distillation column being in fluid communication with the inlet of the second distillation column; wherein the first distillation column has a number of theoretical stripping stages sufficient to remove of the relatively more volatile impurities from the organometallic compound; and wherein the second distillation column has a number of theoretical rectification stages sufficient to obtain purified organometallic compound having a purity of ≥95%.

FIG. 1 is a schematic depiction of a distillation apparatus suitable for use with the process of the invention.

The articles "a" and "an" refer to the singular and the plural. "Alkyl" includes straight chain, branched and cyclic alkyl. "Halogen" refers to fluorine, chlorine, bromine and iodine. The following abbreviations have the following meanings: ppm=parts per million; m=meters; mm=millimeters and ° C.=degrees Celsius. The term "plurality" refers to two or more of an item. The terms "column" and "tower" are used interchangeably. Unless otherwise noted, all amounts are percentages by weight and all ratios are molar ratios. All numerical ranges are inclusive and combinable in any order except where it is clear that such numerical ranges are constrained to add up to 100%.

It will be understood that when an element is referred to as being "on" another element, it can be directly on the other element or intervening elements may be present therebetween. In contrast, when an element is referred to as being "directly on" or "immediately on" another element, there are no intervening elements present.

It will be understood that, although the terms first, second, third, etc. may be used herein to describe various elements, components, regions, layers, zones, portions or sections, these elements, components, regions, layers, zones, portions or sections should not be limited by these terms. These terms are only used to distinguish one element, component, region, layer, zone, portion or section from another element, component, region, layer, zone, portion or section. Thus, a first element, component, region, layer, zone, portion or section discussed below could be termed a second element, component, region, layer, zone, portion or section without departing from the teachings of the present invention.

Furthermore, relative terms, such as "lower" or "bottom" and "upper" or "top," may be used herein to describe one element's relationship to another element as may be illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the figures is turned over, elements described as "below" or "beneath" other elements would then be oriented "above" the other elements. The exemplary terms "below" or "beneath" can, therefore, encompass both an orientation of above and below.

The present invention provides a method of purifying a crude organometallic compound. Crude organometallic compound is conveyed to a distillation apparatus comprising a plurality of distillation columns. The distillation columns are in fluid communication in series. Each distillation column in the apparatus has an upper portion, a center portion and a lower portion. Each upper portion and each lower portion has an outlet. The plurality of distillation columns comprises at least a first distillation column and a second distillation column in fluid communication in series. The outlet in the lower portion of the first column is in fluid communication with the second distillation column. The outlet in the upper portion of the second column is in fluid communication with a container for receiving purified organometallic compound.

In the present process, crude organometallic compound is purified by distillation using an apparatus comprising a plurality of distillation columns. The first distillation column removes relatively lower boiling impurities from the organometallic compound to provide a partially purified organometallic compound. Such partially purified organometallic compound is conveyed to the second distillation column which separates purified organometallic compound from relatively higher boiling impurities. As used herein, the term "relatively lower boiling impurities" or "relatively more volatile impurities" refers to impurities having a boiling point that is lower than the boiling point of the organometallic compound to be purified, that is the impurities are more volatile than the organometallic compound. Likewise, the term "relatively higher boiling impurities" or "relatively less volatile impurities" refers to impurities having a boiling point that is higher than the boiling point of the organometallic compound to be purified, that is, the impurities are less volatile than the organometallic compound. The present process provides a convenient way to purify an organometallic compound which increases the overall yield of purified organometallic compound as compared to conventional distillation processes which discard a significant amount of the desired organometallic compound in the forerun.

It will be appreciated by those skilled in the art that more than two distillation columns may be used, such as 3 or 4 distillation columns or more. When three distillation columns are used, the first and second distillation columns may be used to remove relatively lower boiling impurities while the third column separates purified organometallic compound from relatively higher boiling impurities. For example, crude organometallic compound may be conveyed to a first distillation column and then subjected to conditions sufficient to remove relatively lower boiling impurities. The partially purified organometallic compound can then be conveyed from the lower portion of the first distillation column to the second distillation column, where the partially purified organometallic compound is again subjected to conditions sufficient to remove relatively lower boiling impurities. Next, the further purified organometallic compound is conveyed to the third distillation column and subjected to conditions sufficient to collect purified organometallic compound from the upper portion of the third distillation column. Relatively higher boiling impurities then exit the third distillation column through the outlet in the lower portion. Alternatively when three distillation columns are used, the first distillation column removes relatively lower boiling impurities while the second and third distillation columns separate purified organometallic compound from relatively higher boiling impurities. For example, crude organometallic compound may be conveyed to a first distillation column and then subjected to conditions sufficient to remove relatively lower boiling impurities. The partially purified organometallic compound can then be conveyed from the lower portion of the first distillation column to the second distillation column, where the partially purified organometallic compound is subjected to conditions sufficient to convey further purified organometallic compound from the upper portion of the second distillation column to the third distillation column. Next, the further purified organometallic compound is again subjected to conditions sufficient to collect purified organometallic compound from the upper portion of the third distillation column. Relatively higher boiling impurities exit the second and third distillation columns through the outlet in the lower portion of each of the second and third distillation columns. It will be appreciated by those skilled in the art that 4 or more distillation columns may be used. For example, when 4 distillation columns are used, one, two or three distillation columns may be used to remove relatively lower boiling impurities from the desired organometallic compound, and one, two or three distillation columns may be used to separate the purified organometallic compound from relatively higher boiling impurities, as discussed above. Two distillation columns are preferred.

FIG. 1 is a schematic diagram of a distillation apparatus 10 suitable for use with the process of the invention having a first distillation column 15 having a lower portion 16 and an upper portion 17. First distillation column 15 may optionally contain mass transfer devices, not shown. Crude organometallic compound is conveyed to first distillation column 15 by way of inlet 20. First distillation column 15 has outlet 25 located in upper portion 17 and outlet 30 located in lower portion 16. Optionally, first distillation column 15 may utilize a stripping gas, which enters first distillation column 15 by way of an inlet (not shown) in lower portion 16 and exits by way of outlet 25. Alternatively, a stripping gas may be co-fed with the crude organometallic compound into first distillation column 15 by way of inlet 20. Outlet 30 is in fluid communication with inlet 31 in second distillation column 35. Second distillation column 35 may optionally contain mass transfer devices, not shown, and has an outlet 40 located in upper portion 37 and an outlet 50 located in lower portion 36. Outlet 40 is in fluid communication with receiver 45.

In operation, crude organometallic compound is conveyed to first distillation column 15 by way of inlet 20. In FIG. 1, inlet 20 is shown in the center portion of first distillation column 15, however, inlet 20 can be located at any suitable point in distillation column 15, such as in lower portion 16, upper portion 17, or in the center portion. The particular point at which the crude organometallic compound enters the first distillation column depends on the crude organometallic compound and temperature of the feed stream. First distillation column 15 contains a number of theoretical stripping stages (not shown) sufficient to remove relatively more volatile (lower boiling) impurities. The crude organometallic compound is subjected to conditions in first distillation column 15 sufficient to remove relatively lower boiling impurities (as compared to the desired organometallic compound) from the organometallic compound. Such relatively lower boiling impurities exit first distillation column 15 through outlet 25 in upper portion 17. Partially purified organometallic compound is then conveyed by way of outlet 30 in lower portion 16 to second distillation column 35. Second distillation column 35 contains a number of theoretical rectification stages (not shown) sufficient to obtain purified organometallic compound. The partially purified organometallic compound enters second distillation column 35 through inlet 31 which may be located at any suitable point, such as in lower portion 36, upper portion 37, or in the center portion, which is easily determined by one skilled in the art according to the particular apparatus design. In FIG. 1, inlet 31 is shown in the center portion of second distillation column 35. The partially purified organometallic compound is subjected to conditions in second distillation column 35 sufficient to cause purified organometallic compound to exit second distillation column 35 by way of outlet 40. The purified organometallic compound is then collected in receiver 45. Relatively higher boiling impurities exit second distillation column 35 through outlet 50 in lower portion 36.

Each of the plurality of distillation columns, such as first distillation column 15 and second distillation column 35, includes one or more heat transfer portions, not shown in FIG. 1. Such heat transfer portion may be present anywhere along the distillation column. For example, the heat transfer portion may be part of the lower portion, the upper portion, the center portion, or a part of any combination of these portions. Such heat transfer portion includes heat exchanges such as condensers, chillers, and heaters. The selection of a specific heat transfer portion, and its location in the distillation column, will depend on the size of the distillation column, the volume of crude organometallic compound to be purified, the temperature required for the particular distillation, and the particular crude organometallic compound to be purified, among other factors known to those skilled in the art. Such selection of the heat transfer portion and its location in the stripping column is within the ability of one skilled in the art.

The distillation columns may be composed of any suitable material which will not react with the organometallic compound to be purified. Suitable materials include, without limitation: glass such as borosilicate glass and Pyrex glass; plastics including perfluorinated plastics such as poly (tetrafluoroethylene); quartz; or metal. Metals are preferred, and particularly preferred metals include, without limitation, nickel alloys, titanium and stainless steels. Suitable stainless steels include, but are not limited to, 304, 304 L, 316, 316 L, 321, 347 and 430. Suitable nickel alloys include, but are not limited to, Inconel, Monet, and Hastelloy corrosion-resistant alloys. Each distillation column may be composed of a mixture of materials, such as glass-lined stainless steel. The choice of suitable material for the distillation column is well within the ability of those skilled in the art.

The dimensions of the distillation columns 15 and 35 are not critical. Such columns may have any suitable height and diameter. The choice of such height and diameter will depend on the volume of the crude organometallic compound to be purified, the boiling point differences between the organometallic compound and the impurities present, and any packing material used, among other factors within the ability of those skilled in the art. The column height is influenced by the selection of any packing material used. Typical heights range from 2 to 30 m, preferably from 2.5 to 25 m, more preferably from 2.5 to 20 m, still more preferably from 3 to 15 m, and most preferably from 3 to 12 m. Particularly preferred heights are 2, 2.5, 3, 3.5, 4, 4.5, 5, 6, 7, 8, 9, 9.5, 10, 12, and 15 m. The diameter of the column used depends on the capacity of the column desired. Typical diameters range from 20 mm to 3 m, preferably 20 mm to 2 m, more preferably from 20 mm to 1 m, still more preferably from 20 mm to 500 mm, yet more preferably from 25 to 500 mm, still more preferably from 25 to 400 mm, and most preferably from 25 to 250 mm. Particularly preferred diameters are 25, 30, 35, 40, 50, 60, 75, 100, 125, 150, 175, 200 and 250 mm. It will be appreciated by those skilled in the art that the dimensions of each of the plurality of distillation columns may be the same or different.

Each distillation column may optionally contain any suitable mass transfer devices which will not react with the organometallic compound. Preferably, each column contains mass transfer devices. Such mass transfer devices may be random packing, structured packing, trays or a combination thereof. The random packing material may be any of a wide variety of shapes, such as, but not limited to, baffles, beads, rods, tubes, horseshoes, plates, rings, saddles, discs, saucers, or any other suitable form such as aciform, cruciform, and helicoids (coils and spirals). Mixtures of shapes may be used. The size of the random packing material used will depend on a number of considerations, such as the size of the stripping column and the number of theoretical plates desired to separate impurities from the organometallic compound. Suitable random packing material may have a wide variety of sizes (e.g., diameters), such as 2 mm or greater. A suitable range of sizes for the random packing material is from 2 to 50 mm in diameter. Structured packing material includes wire gauze, corrugated plates, monolithic honeycombs, grids, and the like. The wire gauze may be woven or knitted and may be perforated and/or corrugated. Corrugated plates may optionally be perforated and/or textured. It is preferred that the structured packing is wire gauze. The packing material may be of a uniform size or may be a mixture of sizes. A wide variety of trays may optionally be used in the stripping column of the present invention. Exemplary trays include, without limitation, baffles, floating valves, fixed valves, sieve trays, dual flow trays, co-current flow tray, and the like. Determination of the type, size, quantity and location of the mass transfer devices within each column are well within the ability of one skilled in the art. Mass transfer devices are generally commercially available from a variety of sources, such as Raschig, HAT International, Koch-Glitsch, ACS Separations and Sulzer Chemtech.

The mass transfer devices may be composed of any suitable material, or mixture of materials, that does not react with the organometallic compound to be purified. Exemplary materials useful in plates or packing include, without limitation: ceramics such as alumina, alumina silicates, silica, silicon carbide, and silicon nitride; glass such as borosilicate glass; quartz; graphite balls such as Bucky balls; plastics such as thermoset plastics; and metals such as the stainless steels and nickel alloys described above, as well as titanium and zirconium. Certain metals, such as nickel and chromium, are known to enhance the decomposition of Group 13 organometallic compounds and are best avoided when Group 13 organometallic compounds are purified. However, alloys containing nickel or chromium may be used when Group 13 organometallic compounds are purified.

The first distillation column, that is the column for removing relatively more volatile impurities, contains a number of theoretical stripping stages sufficient to remove of the relatively more volatile impurities from the organometallic compound. Preferably, the first distillation column has ≥30 theoretical stages, and more preferably >30 theoretical stages such as 31 or more theoretical stages. It is further preferred that the first distillation column has a majority of theoretical stripping stages and a minority of theoretical rectification stages. It is further preferred that the ratio of theoretical stripping stages to theoretical rectification stages in the first distillation column is from >1:1 to 20:1, preferably from >1:1 to 10:1, and more preferably from >1:1 to 4:1. For example, when 30 theoretical stages are used in the first distillation column, it is preferred that 20-25 theoretical stripping stages and 5-10 theoretical rectification stages are used. Preferably, the second distillation column, that is the column for obtaining pure organometallic compound, contains a number of theoretical rectification stages sufficient to obtain purified organometallic compound. Preferably, the second distillation column has ≥30 theoretical stages, and more preferably >30 theoretical stages such as 31 or more theoretical stages. It is preferred that the second distillation column has a majority of theoretical rectification stages and a minority of theoretical stripping stages. It is further preferred that the ratio of theoretical rectification stages to theoretical stripping stages in the second distillation column is from >1:1 to 20:1, preferably from >1:1 to 10:1, and more preferably from >1:1 to 4:1. For example, when 30 theoretical stages are used in the second distillation column, it is preferred that 5-10 theoretical stripping stages and 20-25 theoretical rectification stages are used. When more than 2 distillation columns are used, each distillation column used to remove relatively lower boiling impurities should have a design similar to the first distillation column described above and each column used to remove relatively higher boiling impurities should have a design similar to the second distillation column described above. The design of such distillation columns is within the ability of one skilled in the art.

The crude organometallic compound enters the first distillation column by way of the inlet. Typically, the crude organometallic compound is fed into the first distillation column in a vapor-phase, or a liquid-phase, and preferably in a liquid-phase or in a mixture of vapor-phase and liquid-phase. Relatively low-melting point solid organometallic compounds may be purified by appropriately heating the distillation apparatus to a temperature above the melting point of the organometallic compound. For ease of handling, it is preferred that the organometallic compound is conveyed into the first distillation column at a temperature of from 5° C. above its melting point to 5° C. below its boiling point, and more preferably from 10° C. above its melting point to 10° C. below its boiling point. The selection of such temperature depends on the melting point of the organometallic compound to be purified, the boiling points of the impurities to be removed, and on other factors known to those skilled in the art.

Any crude organometallic compound that can be distilled may be purified according to the present process. As used herein, "organometallic compound" refers to a compound having at least one metal-carbon, metal-oxygen, metal-nitrogen or metal-phosphorus bond. As used herein, the term "metal" includes "metalloids." The term "metalloid" as used herein refers to boron (Group 13), germanium (Group 14), phosphorus (Group 15), antimony (Group 15) and arsenic (Group 15). Suitable organometallic compounds contain at least one metal atom chosen from Group 2-Group 15, preferably from Group 3 to Group 15, and more preferably from Group 4 to Group 15. As used herein, Group 14 metals do not include carbon and silicon and Group 15 metals do not include nitrogen. Particularly preferred metals are those in Groups 3, 4, 5, 8, 9, 10, 11, 12, 13, and 15 and even more preferably Groups 4, 8, 11, 12, 13 and 15. Exemplary metal atoms include, without limitation, magnesium, calcium, strontium, scandium, yttrium, lutetium, lawrencium, lanthanum, titanium, zirconium, hafnium, cerium, vanadium, niobium, tantalum, chromium, molybdenum, tungsten, manganese, ruthenium, cobalt, rhodium, iridium, nickel, platinum, palladium, copper, silver, gold, zinc, aluminum, gallium, indium, silicon, germanium, and tin. Preferred metal atoms include magnesium, strontium, scandium, yttrium, lutetium, lawrencium, titanium, zirconium, hafnium, vanadium, niobium, tantalum, molybdenum, tungsten, manganese, ruthenium, cobalt, iridium, nickel, platinum, palladium, copper, silver, gold, zinc, aluminum, gallium, indium, germanium, antimony and arsenic. It is more preferred that the metal atom is magnesium, scandium, yttrium, lutetium, lawrencium, titanium, zirconium, hafnium, niobium, tantalum, molybdenum, tungsten, ruthenium, cobalt, iridium, nickel, platinum, palladium, copper, silver, gold, aluminum, gallium, indium, germanium, antimony and arsenic and even more preferred are magnesium, zirconium, hafnium, niobium, tantalum, molybdenum, tungsten, ruthenium, cobalt, iridium, nickel, copper, aluminum, gallium, indium, germanium, antimony and arsenic, and yet more preferred are magnesium, zirconium, hafnium, aluminum, gallium, indium, germanium, antimony and arsenic.

Suitable organometallic compounds that may be purified according to the present process are any which can be distilled. Such compounds may be liquids at room temperature (25° C.) or compounds that are solid at room temperature and have relatively low melting points (≤100° C.). Preferred organometallic compound are those having a melting point ≤100° C., more preferably ≤80° C., still more preferably ≤75° C., yet more preferably ≤60° C., and even more preferably ≤50° C.

Preferred organometallic compounds that can be purified according to the present process are: metallocenes; cyclopentadienyl compounds of transition metals; methylaluminoxanes; dimethylamido compounds of Group 13-Group 15 metals; ($C_1$-$C_6$)alkyl compounds of Group 13 to Group 15 metals; ($C_1$-$C_4$)alkoxides of transition metals and metals of Groups 13-15; β-diketonate compounds of transition metals and lanthanide metals; and amidinate compounds of copper and cobalt. Metallocenes are metal sandwich compounds having 2 cyclopentradienyl groups. Cyclopentadienyl compounds of transition metals include compounds containing a transition metal and at least one group chosen from cyclopendienyl, methylcyclopentadienyl, and pentamethylcyclopentadienyl. Preferred alkoxides include methoxides, ethoxides, propoxides, butoxides, and mixtures thereof. The ($C_1$-$C_6$) alkyl compounds of Group 13 to Group 15 metals include the mon-, di- and tri-($C_1$-$C_6$)alkyl compounds of Group 13 and Group 15 metals, and the mono-, di-, tri- and terta-($C_1$-$C_6$) alkyl compounds of Group 14 metals. Preferred alkyl groups are methyl, ethyl, propyl, butyl, and combinations thereof. The β-diketonate compounds of transition metals and lanthanide metals may optionally have another ligand, such as hexafluoroacetonylacetonate ("hfac"), in order to make the β-diketonate compound a liquid. Exemplary amidinate compounds of copper and cobalt are those disclosed in International Patent Application WO 2004/046417.

More preferred organometallic compounds are: trialkyl indium compounds such as trimethyl indium, triethyl indium, tri-n-propyl indium, tri-iso-propyl indium, dimethyl iso-propyl indium, dimethyl ethyl indium, dimethyl tert-butyl indium, methyl di-tert-butyl indium, methyl di-isopropyl indium, and tri-tertiarybutyl indium; trialkyl indium-amine adducts; trialkyl indium-trialkyl-phosphine adducts such as trimethyl indium-trimethyl phosphine adduct; trialkyl gallium compounds such as trimethyl gallium, triethyl gallium, tri-iso-propyl gallium, tri-tert-butyl gallium, dimethyl iso-propyl gallium, diethyl tert-butyl gallium, methyl di-iso-propyl gallium, dimethyl tert-butyl gallium, dimethyl neo-pentyl gallium, and methyl ethyl iso-propyl gallium; trialkyl gallium-amine adducts; trialkyl gallium-phosphine adducts; trialkylaluminum compounds such as trimethyl aluminum, triethyl aluminum, tri-n-propyl aluminum, tri-iso-propyl aluminum, tri-tert-butyl aluminum, dimethyl iso-propyl aluminum, dimethyl ethyl aluminum, dimethyl tert-butyl aluminum, methyl di-tert-butyl aluminum, and methyl di-iso-propyl aluminum; metal beta-diketonates such as beta-diketonates of hafnium, zirconium, tantalum and titanium; and metal amidinates such as amidinates of copper and cobalt.

The crude organometallic compound enters the first distillation column. The crude organometallic compound is subjected to conditions sufficient to remove relatively lower boiling impurities. Such conditions are within the ability of one skilled in the art and include maintaining the first distillation column at a temperature above the boiling point of the relatively lower boiling impurities, and providing a reflux ratio of ≥45:1 reflux to distillate. Preferably, the reflux ratio is ≥50:1. Optionally, a stripping gas is used in the first distillation column and enters the column through an inlet in the bottom portion, or alternatively is co-fed with the organometallic compound, and is conveyed upward through the column and exits the column through the outlet in the upper portion. Preferably, a stripping gas is used. The stripping gas is typically inert. Exemplary stripping gases include nitrogen, helium, argon, and methane. Mixtures of stripping gases may be used. The relatively lower boiling impurities exit the first distillation column through the outlet in the upper portion, and are conveyed to a waste stream or other collection device. The organometallic compound, which exits the first distillation column through the outlet in the bottom portion, is partially purified as compared to the organometallic compound entering the first distillation column, in that at least a portion of the relatively lower boiling impurities have been removed. Preferably, ≥90% of the relatively lower boiling impurities have been removed in the first distillation column, more preferably ≥95%, still more preferably ≥97%, and even more preferably ≥99% of the relatively lower boiling impurities have been removed.

Partially purified organometallic compound exits the first distillation column through the outlet in the bottom portion and is conveyed to the second distillation column. The partially purified organometallic compound is subjected to conditions sufficient to obtain purified organometallic compound. That is, the organometallic compound is separated from relatively higher boiling impurities. Such conditions are within the ability of one skilled in the art and include maintaining the second distillation column at a temperature above the boiling point of the organometallic compound, and providing a reflux ratio of ≥1:1 reflux to distillate. Preferably, the reflux ratio is ≥10:1. The purified organometallic compound exits the second distillation column through the outlet in the upper portion, and is conveyed to a receiver. Suitable receivers are any in which the purified organometallic compound can be collected. The collected organometallic compound is purified as compared to the partially organometallic compound entering the second distillation column, in that at least a portion of the relatively higher boiling impurities have been removed. Preferably, ≥90% of the relatively higher boiling impurities have been removed in the second distillation column, more preferably ≥95%, still more preferably ≥97%, and even more preferably ≥99% of the relatively higher boiling impurities have been removed. The relatively higher boiling impurities exit the second distillation column through the outlet in the lower portion, and are conveyed to a waste stream or other collection device.

Purified organometallic compound obtained from the present process has a reduced or greatly eliminated amount of impurities. For example, when the organometallic compound is an organoaluminum compound, particularly an alkylaluminum compound, such as a dialkylaluminum halide or a trialkylaluminum, silicon-containing impurities are removed by the present process. It is preferred that purified organoaluminum compounds are substantially free of silicon-containing impurities. It is further preferred that organogallium compounds are substantially free of aluminum-containing impurities. "Substantially free" means that the purified organometallic compound contains less than 5 ppm of a specific impurity, preferably less than 3 ppm, more preferably less than 2 ppm, even more preferably less than 1 ppm, and yet more preferably less than 0.5 ppm of such impurity. Preferably, the purified organometallic compound contains ≤0.5 ppm of metallic impurities chosen from silicon, germanium and tin.

The present distillation process provides continuous purification of a crude organometallic compound. However, the present process may also be used in a batch purification process. The present distillation process provides organometallic compounds that are ≥90% pure, preferably ≥95% pure, more preferably ≥97% pure, and still more preferably ≥99% pure. It is particularly preferred that the organometallic compound is ≥99.9999% pure. The purified organometallic compound obtained from the present process may be used as is, or may be further purified, if needed, by any suitable process, such as distillation, fractional crystallization, sublimation, and the like. The present distillation process has the advantage of higher overall yield of the organometallic compound as compared to conventional distillation methods because there is no forerun to discard. Preferably, ≤5% of the organometallic compound is lost in the first distillation column. This represents a significant decrease in the loss of organometallic compound as compared to conventional distillation procedures where up to 30-40% of the organometallic compound is discarded in the forerun. Preferably, the purified organometallic compound is obtained in ≥90% overall yield, and more preferably ≥95%.

The purified organometallic compounds of the present invention may be used in a variety of applications that demand the use of high purity organometallic compounds, such as in certain catalyst applications and in the manufacture of electronic devices such as light emitting diodes or other semiconductor applications. The present purified organometallic compounds may also be used as intermediates in the preparation of other organometallic compounds.

EXAMPLE 1

A feed stream containing approximately 15-20% trimethylgallium ("TMG") by weight with balance being hydrocarbon solvent and mixture of aluminum chloride complexes was introduced on a continuous basis to a first distillation column at 95-100° C. at a flow rate of approximately 55 units/hour. The first distillation column contained ≥30 theoretical stages, with a majority of theoretical stripping stages and a minority of theoretical rectification stages, a stripping and rectification bed. The first distillation column was operated at a constant temperature and pressure and an overhead stream sufficient to remove the majority of relatively higher boiling impurities with approximately 0.5 units/hour flow was drawn off from the upper portion of the column. The overhead was refluxed sufficiently to result in a greater than 3 to one reflux to feed ratio. The lower portion of the tower was operated at a constant temperature and level with the addition of heat and a continuous bottoms drawoff of the residual feed. The bottoms draw off, which included the TMG, was sent to a second distillation column. The second distillation column also contained ≥30 theoretical stages, with a majority of rectification stages and a minority of stripping stages. The second distillation column was operated at constant pressure and had a reflux to feed ratio of more than 3 to 1. The bottoms stream from the second distillation column, which contained relatively less volatile impurities as compared to TMG, was continuously removed and the bottoms temperature was maintained constant. A continuous overhead product stream of high purity TMG was drawn off from the upper portion of the second distillation column. The overall yield of the purified TMG was >85%. Analysis of the purified TMG showed it to be >99% pure. The TMG was analyzed by inductively coupled plasma ("ICP") spectroscopy for various metals, with each metal being less than the limit of detection ("LOD"). Specifically, the TMG contained <0.3 ppm Al, <0.07 ppm Si, <0.9 ppm Ge, and <5.4 ppm Sn. The TMG was also analyzed by $^1$H-NMR (400 MHz, 48 minute acquisition time) and found to have no detectable hydrocarbon impurities (LOD=10 ppm). This distillation system was operated successfully for more than 24 hours.

EXAMPLE 2

The procedure of Example 1 was repeated and TMG was obtained in an overall yield of >93% and the TMG had a purity of >99%.

EXAMPLE 3

The procedure of Example 1 is repeated except that TMG is replaced with triethyl gallium.

EXAMPLE 4

The procedure of Example 1 is repeated except that TMG is replaced with triethyl aluminum.

EXAMPLE 5

The procedure of Example 1 is repeated except that TMG is replaced with trimethyl aluminum.

EXAMPLE 6

The procedure of Example 1 is repeated except that TMG is replaced with trimethyl aluminum-tripropylamine adduct.

EXAMPLE 7

The procedure of Example 1 is repeated except that TMG is replaced with triethyl indium adduct.

EXAMPLE 8

The procedure of Example 1 is repeated except that TMG is replaced with dimethyl zinc.

EXAMPLE 9

The procedure of Example 1 is repeated except that TMG is replaced with trimethyl antimony.

EXAMPLE 10

The procedure of Example 1 is repeated except that TMG is replaced with trimethyl arsenic.

EXAMPLE 11

The procedure of Example 1 is repeated except that TMG is replaced with trimethyl bismuth, and similar yields and purity are expected.

What is claimed is:
1. A method of continuously purifying an organometallic compound comprising:
   (a) providing a distillation apparatus comprising a first column and a second column, each column having an upper portion and a lower portion;
   (b) providing a crude organometallic compound to be purified to the first distillation column;
   (c) subjecting the organometallic compound in the first distillation column to conditions sufficient to remove relatively more volatile impurities from the upper portion of the first distillation column;
   (d) conveying the organometallic compound from the lower portion of the first distillation column to the second distillation column; and
   (e) subjecting the organometallic compound in the second distillation column to conditions sufficient to obtain purified organometallic compound from the upper portion of the second distillation column;
wherein the first distillation column has a number of theoretical stripping stages sufficient to remove of the relatively more volatile impurities from the organometallic compound;
wherein the second distillation column has a number of theoretical rectification stages sufficient to obtain purified organometallic compound; and
wherein the obtained purified organic compound has a purity of ≥95%.

2. The method of claim 1 wherein the purified organometallic compound is obtained in an overall yield of ≥90%.

3. The method of claim 2 wherein the purified organometallic compound is obtained in an overall yield of ≥95%.

4. The method of claim 1 wherein the first distillation column has ≥30 theoretical stages.

5. The method of claim 1 wherein the second distillation column has ≥30 theoretical stages.

6. The method of claim 1 wherein the organometallic compound comprises a Group 13 metal.

7. The method of claim 6 wherein the organometallic compound is trimethyl gallium or triethyl gallium.

8. The method of claim 1 wherein the first distillation column further comprises an outlet and a stripping gas that is conveyed upward through the column and exits the first column through the outlet.

9. The method of claim 1 wherein ≥97% of relatively more volatile impurities are removed from the organometallic compound in the first distillation column.

10. The method of claim 1 wherein the first distillation column has a reflux ratio of ≥45:1.

11. The method of claim 1 wherein the second distillation column has a reflux ratio of ≥10:1.

12. A method of continuously purifying an organometallic compound comprising:
(a) providing a distillation apparatus comprising a first column and a second column, each column having an inlet, an upper portion, a lower portion, and an outlet;
(b) providing a crude organometallic compound to be purified to the first distillation column;
(c) subjecting the organometallic compound in the first distillation column to conditions sufficient to remove ≥97% of relatively more volatile impurities from the upper portion of the first distillation column;
(d) conveying the organometallic compound from the lower portion of the first distillation column to the second distillation column; and
(e) subjecting the organometallic compound in the second distillation column to conditions sufficient to obtain purified organometallic compound from the upper portion of the second distillation column;
wherein the first distillation column has a number of theoretical stripping stages sufficient to remove of the relatively more volatile impurities from the organometallic compound;
wherein the second distillation column has a number of theoretical rectification stages sufficient to obtain purified organometallic compound; and
wherein the obtained purified organic compound has a purity of ≥95%.

13. The method of claim 12 wherein the organometallic compound comprises a Group 13 metal.

14. The method of claim 13 wherein the organometallic compound is trimethyl gallium or triethyl gallium.

15. The method of claim 12 wherein the first distillation column further comprises a stripping gas that is conveyed upward through the column and exits the first column through the outlet.

16. The method of claim 12 wherein the first distillation column has a reflux ratio of ≥45:1.

17. The method of claim 12 wherein the second distillation column has a reflux ratio of ≥10:1.

18. The method of claim 12 wherein the first distillation column has a ratio of theoretical stripping stages to theoretical rectification stages of from >1:1 to 20:1.

19. The method of claim 12 wherein the second distillation column has a ratio of theoretical rectification stages to theoretical stripping stages of from >1:1 to 20:1.

* * * * *